United States Patent [19]

Poole et al.

[11] Patent Number: 4,577,506

[45] Date of Patent: Mar. 25, 1986

[54] ULTRASONIC SCANNING PROBE

[75] Inventors: Michael J. Poole, Abingdon; Michael J. Crook, Faringdon, both of England

[73] Assignee: United Kingdom Atomic Energy Authority, London, England

[21] Appl. No.: 617,544

[22] Filed: Jun. 5, 1984

[30] Foreign Application Priority Data

Jun. 24, 1983 [GB] United Kingdom ................ 8317247

[51] Int. Cl.⁴ .......................................... G01N 29/04
[52] U.S. Cl. .......................................................... 73/633
[58] Field of Search ........................ 73/633, 629, 644; 128/660; 310/334, 336

[56] References Cited

U.S. PATENT DOCUMENTS

| | | | |
|---|---|---|---|
| 2,592,134 | 4/1952 | Firestone | 73/629 |
| 2,697,936 | 12/1954 | Farrow | 73/644 |
| 3,175,106 | 3/1965 | Sansom et al. | 73/644 |
| 3,512,400 | 5/1970 | Lynnworth | 73/629 |
| 4,020,679 | 5/1977 | Barry | 73/629 |
| 4,300,217 | 11/1981 | Ballinger | 73/633 |

FOREIGN PATENT DOCUMENTS

| | | | |
|---|---|---|---|
| 0003658 | 8/1979 | European Pat. Off. | 73/633 |
| 0051927 | 5/1982 | European Pat. Off. . | |
| 0102176 | 3/1984 | European Pat. Off. . | |
| 2008754 | 6/1979 | United Kingdom . | |
| 2010484 | 6/1979 | United Kingdom . | |

Primary Examiner—Stephen A. Kreitman
Attorney, Agent, or Firm—William R. Hinds

[57] ABSTRACT

An ultrasonic scanning probe 10 for inspecting structures for internal defects and providing a plan position display comprises a transducer 70 mounted within a block 12 of ultrasonically absorbent material, such as polyethylene, adjacent to a window 30 which may be placed in contact with a surface of the structure. The block 12 is turnable about a rotation axis normal to the window 30, while the transducer 70 is oriented at an angle to the axis so as to scan a sector of the surface as the block 12 is turned, and an attenuating coupling medium 160 occupies the space between the transducer 70 and the window 30. The scanning probe 10 may be used in wet or dry situations.

8 Claims, 1 Drawing Figure

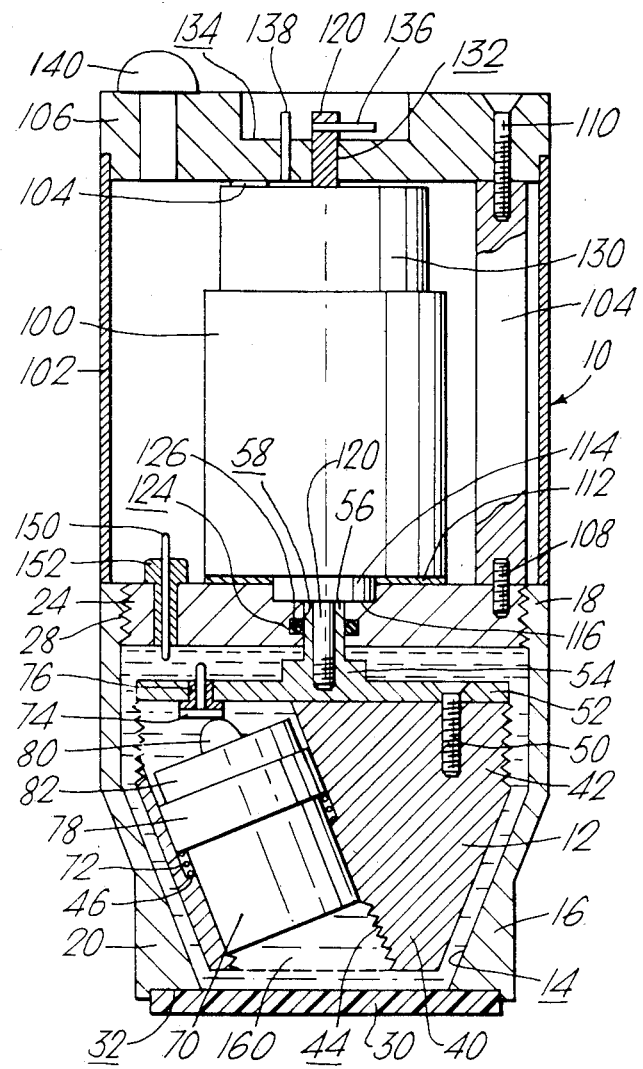

ULTRASONIC SCANNING PROBE

FIELD OF THE INVENTION

This invention relates to ultrasonic instruments for inspecting structures for internal defects.

BACKGROUND OF THE INVENTION

Known instruments such as that described in British patent specification No. 1482 077 incorporate a transducer which when energised emits a pulse of ultrasonic waves, the waves propagating through a coupling medium to the surface of the structure under inspection. The transducer is set far enough from the surface to give a long reverberation time between successive echoes from the surface, echoes from defects within the structure being observed after the first surface echo and before the next reverberation. The coupling medium preferably absorbs little of the wave energy so as not to attenuate the pulse.

British Patent Specification No. 2 010 484 describes an ultrasonic scanner including five transducers rotatably supported, and energised in succession, so as to send an ultrasonic beam onto a fixed plane reflector and so to scan the beam across a sector. The scanned sector lies in a plane substantially perpendicular to the surface against which the probe is placed and is centred about an axis below but parallel to the surface. The scanner therefore provides a cross-sectional display rather than a plan position display of defects below the surface.

FEATURES AND ASPECTS OF THE INVENTION

According to the present invention there is provided an ultrasonic scanning probe comprising, a casing having at one end an ultrasonically-transparent window, a block of ultrasonically-absorbent material close-fitting within the casing and close to the window, and having an axis of rotation which passes through the centre of the window, a transducer mounted within the block in a hole extending from the window at an angle to the axis of rotation of the block, an attenuating coupling medium between the transducer and the window, means for turning the block about the axis of rotation, and means for energising the transducer to emit ultrasonic waves so as to scan a sector centred on the axis of rotation.

Preferably the hole through the block is such that the transducer fits tightly inside the hole. The preferred material for the block is polyethylene, and preferably the outside surface of the block and the surface of the hole are grooved or corrugated to minimise specular reflection of ultrasonic waves.

The invention will now be described by way of example only and with reference to the accompanying drawing, which shows a medial sectional view of a scanning probe.

DESCRIPTION OF PREFERRED EMBODIMENTS

A scanning probe 10 comprises a polyethylene holder block 12 inside a chamber 14 defined by a hollow brass open-ended housing 16, a circular mounting plate 24 threaded around its periphery and engaging in a corresponding internally threaded portion 28 at the upper end 18 (as shown) of the housing 16, and a circular ultrasonically-transparent rubber window 30 glued around its perimeter onto an internal circumferential flange 32 at the lower end 20 of the housing 16. The holder block 12 fits closely inside the housing 16, the gap between the holder block 12 and the housing 16 being about 1 or 2 mm.

The holder block 12 comprises a truncated conical portion 40 of cone angle 22 degrees (i.e. between cone surface and axis) and a coaxial cylindrical portion 42 extending from the wider end of the conical portion 40. A cylindrical hole 44 with a step 46 in the bore extends through the block 12 from one end to the other, being wider at the upper end. The axis of the hole 44 is at an angle of 22 degrees to the axis of the block 12. The axes of the hole 44 and of the block 12 cross at the centre of the window 30. The cylindrical portion 42 is attached by three countersunk screws 50 (only one of which is shown) to a circular plate 52 with a hollow internally threaded central boss 54 from which extends a short hollow axle 56 locating in a hole 58 through the centre of the mounting plate 24. A generally cylindrical transducer 70 is located within the hole 44 through the block 12 and is a tight fit therein, electrical connections to the transducer 70 being made by means of a beryllium copper spring 72 and a brass plunger 74, each of which extends through a respective insulating sleeve 76 through a hole in the plate 52 (only that for the plunger 74 being shown). The spring 72 consists of three turns around the transducer 70 between the step 46 and one side of a circumferential contact strip 78 around the transducer 70, and a straight wire (not shown) extending along a groove (not shown) in the wall of the hole 44 adjacent to the contact strip 78 and then through the respective sleeve, while a terminal 80 at the upper end 82 of the transducer 70 abuts the plunger 74, being resilient biassed into contact by the spring 72.

The curved surfaces of the conical portion 40 and the cylindrical portion 42 of the holder block 12, and the surface of the hole 44 below the transducer 70, are corrugated by parallel grooves about 2.5 mm apart and 1.5 mm deep. The grooves on the surface of the hole 44 run helically, as do the grooves on the cylindrical portion 42, while the grooves on the conical portion 40 run parallel to the axis of the block 12.

The scanning probe 10 also incorporates an electric torque-motor 100, within a tubular case 102 attached to the mounting plate 24 by three equally spaced locating pillars 104 (only two of which are shown) and a circular cap 106. The pillars 104 are attached to the mounting plate 24 by grub screws 108, and to the cap 106 by countersunk screws 110 (only one of each being shown). The cap 106 is partly relieved around its periphery so as to locate accurately the case 102. A neoprene rubber gasket 112 is sandwiched between the lower end of the motor 100 and the mounting plate 24. A central boss 114 on the motor 110 locates in a central recess 116 in the mounting plate 24, and a shaft 120 extends from the boss 114 of the motor 100 through the hollow axle 56 to engage by means of a screw thread in the hollow boss 54 of the plate 52. The shaft 120 of the motor 100 is thus coaxial with the axis of the holder block 12. The hole 58 through the mounting plate 24 incorporates a circumferential groove 124 to accommodate an O-ring 126 through which the axle 56 passes.

The shaft 120 also extends upwardly from the motor 100, through a potentiometer 130 mounted on the upper end of the motor 100, and passes through a hole 132 in the cap 106, terminating in a recess 134 in the cap 106. A pin 136 passes through the shaft 120, lying in the plane defined by the axes of the block 12 and of the hole 44, and so indicating to an operator the orientation of the transducer 70. A stop pin 138 is mounted in the recess 134 adjacent to the shaft 120 so as to prevent rotation of the shaft 120 when the pin 136 contacts the stop pin 138.

Electrical connection to the scanning probe 10 is by two cables (not shown) passing through respective cable clamps 140 (only one of which is shown) through the cap 106. A cable having five wires provides two wires for the motor 100 and three wires for the potentiometer 130. A coaxial cable is connected to the transducer 70 via two connector pins 150 passing through polytetrafluorethylene insulators 152 (only one of each being shown) in the mounting plate 24. From the lower ends of the pins 150 a coiled shielded wire (not shown) leads to the upper ends of the brass plunger 74 with its shield connected to the upper end of the spring 72, so allowing for turning of the plate 52 relative to the mounting plate 24.

A screw plug (not shown) in the mounting plate 24 enables the chamber 14 to be filled with castor oil 160 under vacuum after assembly of the scanning probe 10.

In one mode of use of the scanning probe 10, the window 30 is held against a surface of a structure (not shown) so that the axis of the holder block 12 is normal to the surface. The surface may be covered with a thin layer of a coupling medium such as water, or the structure and the probe 10 may be immersed in water. The transducer 70 is excited so as to emit pulses of ultrasonic compression waves down the hole 44, through the castor oil 160 and the window 30, so as to be incident on the surface at an angle of incidence of 22°. At this angle of incidence, in a steel structure compression waves cannot enter the structure and shear waves are created. Signals reflected or scattered by defects within the structure return to the transducer 70 by the same route, and are received by the transducer 70. In addition the motor 100 is energised to turn the holder block 12 and transducer 70 to and fro between predetermined positions, so as to examine the structure for defects within a sector centred on the axis of the holder block 12.

An electronic circuit (not shown) is also provided to determine from the reading of the potentiometer 130 the orientation of the transducer 70, and to display the position of any defects, detected by received signals, on a plan position indicator.

The distance between the transducer 70 and the window 30 is such that any echoes reverberating between the transducer 70 and the surface of the structure are rapidly attenuated both by losses at each reflection and by attenuation in the oil 160. No signals can be detected from defects within the structure until the reverberating echoes have died away. Subsequently, signals can be detected from defects up until the next time the transducer 70 is excited. In use of the scanning probe 20 under water in this mode it will be understood that the window 30 may be spaced away from the surface of the structure by up to about 5 mm.

In an alternative mode of use, the scanning probe 10 is operated under water, the distance between the window 30 and the surface of the structure being 150 mm or more. Signals from defects within the structure can be detected after the first echo from the surface of the structure and before the next reverberating echo.

Castor oil 160 has about the same acoustic impedance as water, so that reflections from the window 30 are minimised when water occupies the space outside the window 30, but castor oil 160 provides much more attenuation than does water. For ultrasonic waves at 1 MHz the attenuations are about 1 dB/cm and 0.0025 dB/cm respectively. Hence waves reverberating in the castor oil 160 are rapidly attenuated. Polyethylene, of which the holder block 12 is made, is a strongly attenuating solid, with an attenuation of about 4.7 dB/cm. Consequently any ultrasonic waves approaching the transducer 70 from directions other than along the axis of the hole 44 will be diffusely scattered by the corrugated surfaces of the holder block 12, and attenuated by their passage through either castor oil 160 or polyethylene. Waves propagating around the sides of the holder block 12 will reverberate in the narrow gap between the holder block 12 and the housing 16, and will be diffusely scattered at each reflection from the holder block 12, and so be attenuated. The transducer 70 is thus shielded from stray echoes.

It will be understood that the angle between the axes of the holder block 12 and the hole 44 determines the angle of incidence of the ultrasonic compression waves at the surface, and hence the predominant type of waves which propagate within the structure. As explained above, with a steel structure, an angle of incidence of 22° causes mainly shear waves to propagate, and so the scanning probe 10 can be used with structures whether or not they are immersed in water. An alternative holder block (not shown) may be used, differing from the holder block 12 in that the angle between the axes of the block and of the hole is 27° (which is above the critical angles for both longitudinal and shear waves), in which case only surface waves will propagate in the surface of the structure. Such a holder block cannot be used with a structure whose surface is under water as surface waves are rapidly attenuated by mode conversion when propagating in a surface in contact with a liquid. Yet again an alternative holder block (not shown) may be used differing from the holder block 12 in that the angle between the axes is 12° (below the critical angle for longitudinal waves) in which case longitudinal waves will propagate in the structure. At certain angles of incidence plate waves will propagate in the structure, and holder blocks (not shown) may be used differing from the holder block 12 in that the angle between the axes is such as to cause propagation of a desired plate wave mode in the structure.

It will also be understood that the motor 100 may be controlled so as to scan the orientation of the transducer 70 between any two predetermined directions, lying within the limits at which the pin 136 hits the stop pin 138.

It will be appreciated that the housing 16 may also be of an attenuating solid, and that the inside surfaces of the housing 16 may be corrugated or grooved to prevent specular reflection of ultrasonic waves.

We claim:

1. An ultrasonic scanning probe comprising, a casing having at one end an ultrasonically-transparent window, a block of ultrasonically-absorbent material close-fitting within the casing and close to the window, having an axis of rotation which passes through the centre of the window and defining a hole extending from the window at an angle to the axis of rotation of the block, the fit being such as to define a narrow gap between the block and the casing of width not more than about 2 mm, a transducer mounted within the hole, an attenuating coupling medium filling the gap and the space between the transducer and the window, so as to scan a sector centred on the axis of rotation.

2. A probe as claimed in claim 1 wherein the hole through the block is such that the transducer fits tightly inside the hole.

3. A probe as claimed in claim 1 wherein an outside surface of the block and a surface of the hole are roughened, so as to inhibit specular reflection of ultrasonic waves from the said surfaces of the block and the hole.

4. A probe as claimed in claim 1 further comprising means for indicating the orientation of the transducer.

5. A probe as claimed in claim 1 wherein the angle to the axis of the block is such that the transducer, when energised, causes shear waves to propagate in the structure.

6. A probe as claimed in claim 1 wherein the angle to the axis of the block is such that the transducer, when energised, causes surface waves to propagate in the structure.

7. A probe as claimed in claim 1 wherein the angle of the axis of the block is such that the transducer when energised causes longitudinal waves to propagate in the structure.

8. A probe as claimed in claim 1 wherein the angle to the axis of the block is such that the transducer when energised causes plate waves to propagate in the structure.

* * * * *